(12) United States Patent
Wang et al.

(10) Patent No.: US 9,717,712 B2
(45) Date of Patent: Aug. 1, 2017

(54) COMBINATIONS COMPRISING TRICYCLOHEXADECAHEXAENE DERIVATIVES FOR USE IN THE TREATMENT OF HEPATITIS C VIRUS

(71) Applicant: BRISTOL-MYERS SQUIBB COMPANY, Princeton, NJ (US)

(72) Inventors: Alan Xiangdong Wang, Wallingford, CT (US); Omar D. Lopez, Wallingford, CT (US); Yong Tu, Cheshire, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/904,817

(22) PCT Filed: Jul. 15, 2014

(86) PCT No.: PCT/US2014/046685
§ 371 (c)(1),
(2) Date: Jan. 13, 2016

(87) PCT Pub. No.: WO2015/026454
PCT Pub. Date: Feb. 26, 2015

(65) Prior Publication Data
US 2016/0166547 A1 Jun. 16, 2016

Related U.S. Application Data

(60) Provisional application No. 61/847,388, filed on Jul. 17, 2013.

(51) Int. Cl.
A61K 31/415 (2006.01)
A61K 31/4184 (2006.01)
A61K 31/4178 (2006.01)
A61K 38/21 (2006.01)
A61K 31/7056 (2006.01)

(52) U.S. Cl.
CPC ...... A61K 31/4184 (2013.01); A61K 31/4178 (2013.01); A61K 31/7056 (2013.01); A61K 38/21 (2013.01); A61K 38/212 (2013.01)

(58) Field of Classification Search
CPC ................ A61K 31/4184; A61K 31/4178
USPC .................................. 514/394, 397
See application file for complete search history.

(56) References Cited

U.S. PATENT DOCUMENTS

| 5,654,451 | A | 8/1997 | Kari |
|---|---|---|---|
| 7,745,636 | B2 | 6/2010 | Bachand et al. |
| 7,894,996 | B2 | 2/2011 | Rice et al. |
| 8,288,562 | B2 | 10/2012 | Bachand et al. |
| 8,303,944 | B2 | 11/2012 | Bachand et al. |
| 8,492,553 | B2 | 7/2013 | Bachand et al. |
| 8,574,563 | B2 | 11/2013 | Bachand et al. |
| 8,618,153 | B2 | 12/2013 | Bender et al. |
| 8,642,025 | B2 | 2/2014 | Bachand et al. |
| 8,735,398 | B2 | 5/2014 | Lopez et al. |
| 8,846,023 | B2 | 9/2014 | Bachand et al. |
| 8,900,566 | B2 | 12/2014 | Belema et al. |
| 9,006,455 | B2 | 4/2015 | Pack et al. |
| 9,018,390 | B2 | 4/2015 | Bachand et al. |
| 9,227,961 | B2 | 1/2016 | Bachand et al. |
| 9,303,007 | B2 | 4/2016 | Lopez |
| 9,340,520 | B2 | 5/2016 | Lopez et al. |
| 9,561,212 | B2 | 2/2017 | Romine et al. |
| 2010/0158862 | A1 | 6/2010 | Kim et al. |
| 2011/0092415 | A1 | 4/2011 | DeGoey et al. |
| 2011/0206637 | A1 | 8/2011 | Or et al. |
| 2011/0218175 | A1 | 9/2011 | Or et al. |
| 2011/0237636 | A1 | 9/2011 | Belema et al. |
| 2011/0268697 | A1 | 11/2011 | Kim et al. |
| 2012/0302538 | A1* | 11/2012 | Wiles .................. C07D 401/14 514/186 |
| 2013/0071352 | A1 | 3/2013 | Dousson et al. |
| 2013/0072523 | A1 | 3/2013 | Liu et al. |
| 2013/0072690 | A1 | 3/2013 | Chen et al. |
| 2013/0115193 | A1 | 5/2013 | Lavoie et al. |
| 2013/0259832 | A1 | 10/2013 | Lemm et al. |
| 2014/0018389 | A1 | 1/2014 | Lavoie et al. |
| 2014/0205564 | A1 | 7/2014 | Romine et al. |
| 2015/0023913 | A1 | 1/2015 | Hewawasam et al. |
| 2015/0297568 | A1 | 10/2015 | Hewawasam et al. |
| 2015/0322048 | A1 | 11/2015 | Lavoie et al. |
| 2015/0335655 | A1 | 11/2015 | Gao et al. |
| 2016/0067223 | A1 | 3/2016 | Belema et al. |

(Continued)

FOREIGN PATENT DOCUMENTS

| WO | WO94/15909 | 7/1994 |
|---|---|---|
| WO | WO2004/005264 A2 | 1/2004 |
| WO | WO2006/022442 A1 | 3/2006 |
| WO | WO2006093867 A1 | 9/2006 |
| WO | WO2006/133326 A1 | 12/2006 |
| WO | WO2007/031791 A1 | 3/2007 |
| WO | WO2007/058384 A1 | 5/2007 |
| WO | WO2007/076034 A2 | 7/2007 |
| WO | WO2007/077186 A1 | 7/2007 |
| WO | WO 2007/081517 A2 | 7/2007 |
| WO | WO2007/138242 A1 | 12/2007 |
| WO | WO2008/021927 A2 | 2/2008 |
| WO | WO2008/021936 A2 | 2/2008 |
| WO | WO2008021928 A2 | 2/2008 |
| WO | WO 2008/070447 A2 | 6/2008 |
| WO | WO2008/133753 A2 | 11/2008 |
| WO | WO2008/144380 A1 | 11/2008 |

(Continued)

OTHER PUBLICATIONS

Lemm, et al., "Identification of Hepatitis C Virus NS5A Inhibitors," J. Virology, 84, pp. 482-491 (2010).

(Continued)

Primary Examiner — Shengjun Wang
(74) Attorney, Agent, or Firm — Pamela A. Mingo

(57) ABSTRACT

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

12 Claims, No Drawings

(56) References Cited

U.S. PATENT DOCUMENTS

2016/0199355 A1 7/2016 Gao et al.
2016/0311778 A1 10/2016 Bachand et al.

FOREIGN PATENT DOCUMENTS

| | | |
|---|---|---|
| WO | WO2009/020825 A1 | 2/2009 |
| WO | WO2009/020828 A1 | 2/2009 |
| WO | WO2009/102568 A1 | 8/2009 |
| WO | WO2009/102633 A1 | 8/2009 |
| WO | WO2009/102694 A2 | 8/2009 |
| WO | WO 2010/017401 A1 | 2/2010 |
| WO | WO 2010/039793 A1 | 4/2010 |
| WO | WO2010/062821 A1 | 6/2010 |
| WO | WO 2010/065668 A1 | 6/2010 |
| WO | WO2010/065674 A1 | 6/2010 |
| WO | WO2010/065681 A1 | 6/2010 |
| WO | WO2010/075376 A2 | 7/2010 |
| WO | WO2010/091413 A1 | 8/2010 |
| WO | WO2010/094977 A1 | 8/2010 |
| WO | WO2010/096302 A1 | 8/2010 |
| WO | WO2010/096462 A1 | 8/2010 |
| WO | WO2010/096777 A1 | 8/2010 |
| WO | WO2010/099527 A1 | 9/2010 |
| WO | WO2010/111483 A1 | 9/2010 |
| WO | WO2010/111534 A1 | 9/2010 |
| WO | WO2010/111673 A1 | 9/2010 |
| WO | WO2010/117635 A1 | 10/2010 |
| WO | WO2010/117704 A1 | 10/2010 |
| WO | WO2010/117977 A1 | 10/2010 |
| WO | WO2010/120621 A1 | 10/2010 |
| WO | WO2010/120935 A1 | 10/2010 |
| WO | WO2010/122162 A1 | 10/2010 |
| WO | WO2010/132538 A1 | 11/2010 |
| WO | WO2010/132601 A1 | 11/2010 |
| WO | WO2010/138368 A1 | 12/2010 |
| WO | WO2010/138488 A1 | 12/2010 |
| WO | WO2010/138790 A1 | 12/2010 |
| WO | WO2010/138791 A1 | 12/2010 |
| WO | WO2010/144646 A2 | 12/2010 |
| WO | WO2010/148006 A1 | 12/2010 |
| WO | WO2011/004276 A1 | 1/2011 |
| WO | WO2011/009084 A2 | 1/2011 |
| WO | WO2011/015657 A1 | 2/2011 |
| WO | WO2011/015658 A1 | 2/2011 |
| WO | WO2011/026920 A1 | 3/2011 |
| WO | WO2011/028596 A1 | 3/2011 |
| WO | WO2011/031904 A1 | 3/2011 |
| WO | WO2011/031934 A1 | 3/2011 |
| WO | WO2011/046811 A1 | 4/2011 |
| WO | WO2011/050146 A1 | 4/2011 |
| WO | WO2011/054834 A1 | 5/2011 |
| WO | WO2011/059850 A1 | 5/2011 |
| WO | WO2011/059887 A1 | 5/2011 |
| WO | WO2011/060000 | 5/2011 |
| WO | WO2011/066241 A1 | 6/2011 |
| WO | WO2011/068941 A2 | 6/2011 |
| WO | WO2011/075439 A1 | 6/2011 |
| WO | WO2011/075607 A1 | 6/2011 |
| WO | WO2011/075615 A1 | 6/2011 |
| WO | WO2011/079327 A1 | 6/2011 |
| WO | WO2011/081918 A1 | 7/2011 |
| WO | WO2011/082077 A1 | 7/2011 |
| WO | WO2011/087740 A1 | 7/2011 |
| WO | WO2011/091417 A1 | 7/2011 |
| WO | WO2011/091446 A1 | 7/2011 |
| WO | WO2011/091532 A1 | 8/2011 |
| WO | WO2011/109037 A1 | 9/2011 |
| WO | WO2011/112429 A1 | 9/2011 |
| WO | WO2011/119853 A1 | 9/2011 |
| WO | WO2011/119860 A1 | 9/2011 |
| WO | WO2011/119870 A1 | 9/2011 |
| WO | WO2011/127350 A1 | 10/2011 |
| WO | WO2011/146401 A1 | 11/2011 |
| WO | WO2011/149856 A1 | 12/2011 |
| WO | WO2011/150243 A1 | 12/2011 |
| WO | WO2011/153396 A1 | 12/2011 |
| WO | WO2011/154871 A1 | 12/2011 |
| WO | WO2011/156543 A2 | 12/2011 |
| WO | WO2011156578 A1 | 12/2011 |
| WO | WO2012/003642 A1 | 1/2012 |
| WO | WO2012/009394 A2 | 1/2012 |
| WO | WO2012/013643 A1 | 2/2012 |
| WO | WO2012/018325 A1 | 2/2012 |
| WO | WO2012/018534 A2 | 2/2012 |
| WO | WO2012/018829 A1 | 2/2012 |
| WO | WO2012/020036 A1 | 2/2012 |
| WO | WO2012/021591 A1 | 2/2012 |
| WO | WO2012/021704 A1 | 2/2012 |
| WO | WO2012/027712 A2 | 3/2012 |
| WO | WO2012/040389 A2 | 3/2012 |
| WO | WO2012/040923 A1 | 4/2012 |
| WO | WO2012/040924 A1 | 4/2012 |
| WO | WO2012/041014 A1 | 4/2012 |
| WO | WO2012/041227 A1 | 4/2012 |
| WO | WO2012/048421 A1 | 4/2012 |
| WO | WO2012/050848 A1 | 4/2012 |
| WO | WO2012/050850 A1 | 4/2012 |
| WO | WO2012/050918 A2 | 4/2012 |
| WO | WO2012/051361 A1 | 4/2012 |
| WO | WO2012/061552 A1 | 5/2012 |
| WO | WO2012/068234 A2 | 5/2012 |
| WO | WO2012/074437 A2 | 6/2012 |
| WO | WO2012/083043 A1 | 6/2012 |
| WO | WO2012/083048 A2 | 6/2012 |
| WO | WO2012/083053 A2 | 6/2012 |
| WO | WO2012/083058 A2 | 6/2012 |
| WO | WO2012/083059 A1 | 6/2012 |
| WO | WO2012/083061 A2 | 6/2012 |
| WO | WO2012/083170 A1 | 6/2012 |
| WO | WO2012/087596 A1 | 6/2012 |
| WO | WO2012083164 A1 | 6/2012 |
| WO | WO2012087976 A2 | 6/2012 |
| WO | WO2013/098313 A1 | 7/2012 |
| WO | WO2013/098320 A1 | 7/2012 |
| WO | WO2012/116257 A1 | 8/2012 |
| WO | WO2012109080 A1 | 8/2012 |
| WO | WO2012/123298 A1 | 9/2012 |
| WO | WO2012/125926 A2 | 9/2012 |
| WO | WO2012122716 A1 | 9/2012 |
| WO | WO2012/135581 A1 | 10/2012 |
| WO | WO2012/154777 A1 | 11/2012 |
| WO | WO2012162578 A2 | 11/2012 |
| WO | WO2012162580 A2 | 11/2012 |
| WO | WO2012/166716 A2 | 12/2012 |
| WO | WO2012/175581 A1 | 12/2012 |
| WO | WO2013/007106 A1 | 1/2013 |
| WO | WO2013/021337 A1 | 2/2013 |
| WO | WO2013/021344 A1 | 2/2013 |
| WO | WO2013/022810 A1 | 2/2013 |
| WO | WO2013/028953 A1 | 2/2013 |
| WO | WO2013/030750 A1 | 3/2013 |
| WO | WO2013/039876 A1 | 3/2013 |
| WO | WO2013/039878 A1 | 3/2013 |
| WO | WO2013/052362 A1 | 4/2013 |
| WO | WO2013/052369 A1 | 4/2013 |
| WO | WO2013/053657 A1 | 4/2013 |
| WO | WO2013/059278 A2 | 4/2013 |
| WO | WO2013/059630 A1 | 4/2013 |
| WO | WO2013/059638 A1 | 4/2013 |
| WO | WO2013/066753 A1 | 5/2013 |
| WO | WO2013/075029 A1 | 5/2013 |
| WO | WO2013/087743 A1 | 6/2013 |
| WO | WO2013/095275 A1 | 6/2013 |
| WO | WO2013/101550 A1 | 7/2013 |
| WO | WO2013/106520 A1 | 7/2013 |
| WO | WO2013101552 A1 | 7/2013 |
| WO | WO2013/118097 A1 | 8/2013 |
| WO | WO2013/118102 A1 | 8/2013 |
| WO | WO2013/123092 A1 | 8/2013 |
| WO | WO2013/173492 A1 | 11/2013 |
| WO | WO2014/036244 A1 | 3/2014 |
| WO | WO2014/065791 A1 | 5/2014 |
| WO | WO2014/074604 A2 | 5/2014 |
| WO | WO2014/100500 A1 | 6/2014 |

(56) References Cited

FOREIGN PATENT DOCUMENTS

| WO | WO2015/009744 A1 | 1/2015 |
| WO | WO2015/017382 A1 | 2/2015 |
| WO | WO2015/042375 A1 | 3/2015 |
| WO | WO2015/088817 A1 | 6/2015 |
| WO | WO2015/110048 A1 | 7/2015 |
| WO | WO2015/134560 A1 | 9/2015 |
| WO | WO2015/134561 A1 | 9/2015 |
| WO | WO2015/160907 A2 | 10/2015 |

OTHER PUBLICATIONS

Gao, et al., Chemical Genetics Strategy Identifies an HCV NS5A Inhibitor with a Potent Clinical Effect, Nature, 465, pp. 96-100 (2010).

Fridell, et al., "Resistance Analysis of the Hepatitis C Virus NS5A Inhibitor BMS-790052 in an In Vitro Replicon System," Antimicrob. Agents Chemother., 54, pp. 3641-3650 (2010).

Romine, et al. "Inhibitors of HCV NS5A: From Iminothiazolidinones to Symmetrical Stilbenes," ACS Med. Chem. Lett., 2, pp. 224-229 (2011).

O'Boyle, et al., "Development of a Cell-based High-Throughput Specificity Screen Using a HCV/BVDV Dual Replicon Assay," Antimicrob. Agents Chemother., 49, pp. 1346-1353 (2005).

Lemm, et al, "Discovery of Potent NS5A Inhibitors with Dimeric Structures," Antimicrob. Agents and Chemother., 55, pp. 3795-3802 (2011).

Fridell, et al., "Distinct Functions of NS5A in HCV RNA Replication Uncovered by Studies with the NS5A Inhibitor BMS-790052," J Virol., 85, pp. 7312-7320 (2011).

Fridell, et al., "Genotypic and Phenotypic Analysis of Variants Resistant to HCV NS5A Replication Complex Inhibitor BMS-790052: In Vitro and In Vivo Correlations," Hepatology, 54, pp. 1924-1935 (2011).

Nettles, et al., "Multiple ascending dose study to evaluate BMS-790052 a novel NS5A inhibitor in subjects infected with hepatitis C virus genotype 1.," Hepatology, 54, pp. 1956-1966 (2011).

Qiu, et al., "The effects of NS5A inhibitors on NS5A phosphorylation polyprotein processing and localization," J. Gen. Virology, 92, pp. 2502-2511 (2011).

Sun, "Impact of a baseline polymorphism on the emergence of resistance to the HCV NS5A replication complex inhibitor BMS-790052," Hepatology, 55, pp. 1956-1965 (2011).

Wang, et al., "In Vitro Activity of BMS-790052 on Hepatitis C Virus Genotype 4 NS5A, Antimicrob. Agents and Chemother.," 56, pp. 1588-1590 (2012).

Wang, et al., "Hepatitis C virus RNA elimination and development of resistance in replicon cells treated with BMS-790052," Antimicrob. Agents and Chemother., 56, pp. 1350-1358 (2012).

Pelosi, et al. "Effect of NS5A Inhibitor Combinations on HCV Replication In Vitro.,," Antimicrob. Agents and Chemother., 56, pp. 5230-5639 (2012).

Wang, et al., "In vitro Activity of Daclatasvir on Hepatitis C Virus Genotype 3 NS5A," Antimicrob. Agents and Chemother., 57, pp. 611-613 (2013).

* cited by examiner

COMBINATIONS COMPRISING TRICYCLOHEXADECAHEXAENE DERIVATIVES FOR USE IN THE TREATMENT OF HEPATITIS C VIRUS

CROSS-REFERENCE TO RELATED APPLICATIONS

This application claims the benefit of U.S. Provisional Application Ser. No. 61/847,388, filed on Jul. 17, 2013, which is hereby incorporated by reference in its entirety.

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Over the past decade the standard of care for the treatment of chronic HCV employed a combination of pegylated-interferon and ribavirin. The treatment has a non-optimal success rate in achieving sustained viral response (SVR) against the six major HCV genotypes, with a particularly low success rate against genotype 1, and causes numerous side effects. Recently approved drugs targeting the HCV NS3/4A protease (PIs) (Victrelis® and Incivek®) are administered with pegylated-interferon and ribavirin and provide a major improvement in the percentage of patients who experience SVR and the treatment duration required to achieve SVR. However, there is a clear and urgent need to develop additional therapies to combat protease inhibitor resistance, to improve efficacy across all HCV genotypes, and to advance antiviral therapy towards the ultimate goal of an interferon-free cure.

HCV is a positive-stranded RNA virus of approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein is a cofactor for the NS3 protease. The formation of a NS3-NS4A complex is necessary for proper protease activity. The NS3 protein also exhibits nucleoside triphosphatase and RNA helicase activities. NS5A is a multi-functional protein required for viral RNA replication and virion assembly. NS5B (also referred to herein as HCV polymerase) is a RNA-dependent RNA polymerase that is responsible for viral RNA synthesis.

Considerable heterogeneity is found within the nucleotide and encoded amino acid sequence throughout the HCV genome due to the high error rate of the encoded RNA-dependent RNA polymerase which lacks a proof-reading capability. The clinical significance of the genetic heterogeneity of HCV is the propensity for mutations to arise during monotherapy treatment, thus combination therapies with HCV inhibitors that have pan-genotype coverage and act via independent mechanisms are desired.

Compounds which selectively inhibit HCV viral replication and are useful for treating HCV-infected patients are desired. In particular, compounds which effectively inhibit the function of the NS5A protein are desired. The function and the essential role of NS5A protein for HCV replication are described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); M. Gao, et al, *Nature* (2010); C. Rice, et al., WO2006093867.

A method has been described to identify compounds that demonstrate synergistic inhibition of HCV replicon activity when combined with the HCV NS5A inhibitor such as BMS-790052 (PCT/US2011/043785, filed Jul. 13, 2011). In brief, each compound, when tested individually versus some NS5A resistant variants, is essentially inactive or much less active and only has synergistic inhibitory activity when tested in combination with an NS5A-targeting compound. The synergistic compounds were identified using titrations of test compounds in the presence of fixed concentrations of HCV NS5A inhibitors such as BMS-790052.

In a first aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (I):

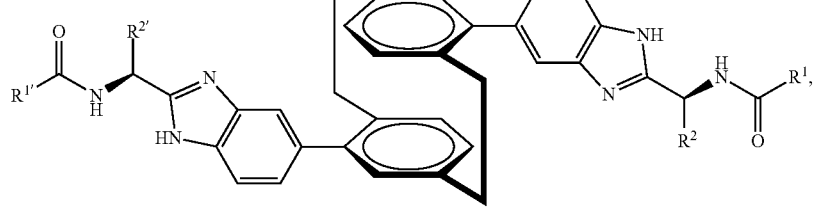

(I)

or a pharmaceutically acceptable salt thereof, wherein $R^{1'}$ and $R^{1'}$ are independently selected from alkoxyalkyl, alkyl, cycloalkyl, and pyranyl, wherein the cycloalkyl and the pyranyl are optionally substituted with one, two, or three substituents independently selected from alkyl, halo, haloalkyl, hydroxy, and hydroxyalkyl; and $R^2$ and $R^{2'}$ are the same or different alkyl groups.

In a first embodiment of the first aspect the present disclosure provides a composition comprising said combination and one or more pharmaceutically acceptable carriers. In a second embodiment said composition comprises one or two additional compounds having anti-HCV activity. In a third embodiment at least one of the additional compounds is an interferon or a ribavirin. In a fourth embodiment the interferon is selected from interferon alpha 2B, pegylated interferon alpha, pegylated interferon lambda, consensus interferon, interferon alpha 2A, and lymphoblastoid interferon tau. In a fifth embodiment said composition comprises one or two additional compounds having anti-HCV activity wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In a second aspect the present disclosure provides a method of treating an HCV infection in a patient, comprising administering to the patient a therapeutically effective amount of a combination of said combination, or a pharmaceutically acceptable salt thereof. In a first embodiment of the second aspect the method further comprises administering one or two additional compounds having anti-HCV activity prior to, after or simultaneously with the combination, or a pharmaceutically acceptable salt thereof. In a second embodiment at least one of the additional compounds is an interferon or a ribavirin. In a third embodiment the interferon is selected from interferon alpha 2B, pegylated interferon alpha, pegylated interferon lambda, consensus interferon, interferon alpha 2A, and lymphoblastoid interferon tau. In a fourth embodiment at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In another aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (II):

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

As used herein, the term "NS5A synergist" refers to a molecule that alone shows a weaker activity against HCV wild type than the NS5A-targeting compound, but when combined with an NS5A-targeting compound shows a greater than three-fold increase in $EC_{50}$ potency than the potency of the NS5A-targeting compound alone.

As used herein, the term "synergistic anti-HCV activity" refers to a greater than three-fold increase in $EC_{50}$ potency than the potency of the NS5A-targeting compound alone.

(II)

or a pharmaceutically acceptable salt thereof, wherein $R^{1'}$ and $R^{1'}$ are independently selected from alkyl and cycloalkyl, wherein the cycloalkyl is optionally substituted with one, two, or three substituents independently selected from alkyl, halo, haloalkyl, hydroxy, and hydroxyalkyl.

As used herein, the term "NS5A-targeting compound", refers to a molecule that inhibits HCV replication for which at least one resistance substitution maps to the NS5A protein and most commonly within, but not limited to, the first 100 residues of NS5A.

The term "alkoxy," as used herein, refers to an alkyl group attached to the parent molecular group through an oxygen atom.

The term "alkoxyalkyl," as used herein, refers to an alkyl group substituted with one, two, or three alkoxy groups.

The term "alkyl," as used herein, refers to a group derived from a straight or branched chain saturated hydrocarbon containing from one to seven carbon atoms.

The term "cycloalkyl," as used herein, refers to a three- to seven-membered monocyclic saturated carbocyclic ring.

The term "halo," as used herein, refers to Cl, Br, F, or I.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace the compounds making up the combination of the present disclosure and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of each compound of the combination, as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of the compounds comprising the combination or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of the combination and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing the compounds of the combination, or pharmaceutically acceptable salts thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidyl-cholines.

The compounds of the combination and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table A below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE A

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |

TABLE A-continued

| Brand Name | Physiological Class | Type of Inhibitor or Target | Source Company |
|---|---|---|---|
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopy-rimidine compounds and salts From WO-2005047288 May 26, 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceutica ls Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharma-ceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |

TABLE A-continued

| Brand Name | Physiological Class | Type of Inhibitor or Target | Source Company |
|---|---|---|---|
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead |
| sofosbuvir | Antiviral | Nucleotide NS5B Polymerase Inhibitor | Gilead |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Achillion |
| asunaprevir | Antiviral | serine protease inhibitor | Bristol-Myers Squibb |
| IDX-719 | Antiviral | NS5A inhibitor | Idenix |
| Ledipasvir | Antiviral | NS5A inhibitor | Gilead |
| GS-5816 | Antiviral | NS5A inhibitor | Gilead |
| Ombitasvir | Antiviral | NS5A inhibitor | Abbvie |
| GSK-2336805 | Antiviral | NS5A inhibitor | GlaxoSmithKline |
| PPI-461 | Antiviral | NS5A inhibitor | Presidio |
| EDP-239 | Antiviral | NS5A inhibitor | Enanta |
| Elbasvir | Antiviral | NS5A inhibitor | Merck |
| IDX-21437 | Antiviral | Nucleotide Polymerase Inhibitor | Idenix |
| Samatasvir | Antiviral | NS5A Inhibitor | Idenix |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT or rt for room temperature or retention time (context will dictate); ret t for retention time; min or mins for minutes; TFA for trifluoroacetic acid; min or mins for minutes; ACN or MeCN for acetonitrile; DCM for dichloromethane; DIEA or DiPEA or DIPEA for diisopropylethylamine; HATU for O-(7-azabenzotriazol-1-yl)-N,N,N',N'-tetramethyluronium hexafluorphosphate; h or hr or hrs for hours; MeOH for methanol; dppf for diphenylphosphinoferrocene; EtOAc for ethyl acetate; OAc for acetate; DMSO for dimethylsulfoxide; TBTU for 2-(1H-benzotriazole-1-yl)-1,1,3,3-tetramethyluronium tetrafluoroborate; Me for methyl; and DMF for N,N-dimethylformamide.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what was believed to be the most useful and readily understood description of its procedures and conceptual aspects.

Starting materials can be obtained from commercial sources or prepared by well-established literature methods known to those of ordinary skill in the art. Acid precursors for the final step can be prepared according to the methods described in U.S. patent application Ser. No. 13/933,495, filed Jul. 2, 2013.

LC/MS Condition 1
Column=Ascentis Express C18, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.4 min; Stop time=4 min
Stop time=4 min
Flow Rate=1 mL/min; Wavelength=220 nm
LC/MS Condition 2
Column=Waters BEH C18, 2.0×50 mm, 1.7 μm
Solvent A=ACN (5%)+H$_2$O (95%) containing 10 mM NH$_4$OAc
Solvent B=ACN (95%)+H$_2$O (5%) containing 10 mM NH$_4$OAc
Start % B=0; Final % B=100
Gradient time=3 min
Flow Rate=1 mL/min
Wavelength=220 nm
Temperature=50° C.
LC/MS Condition 3
Column: Waters Phenomenex C18, 2.0×30 mm, 3 μm particle
Mobile Phase A: 10% MeOH:90% Water:0.1% TFA
Mobile Phase B: 90% MeOH:10% Water:0.1% TFA
Gradient: 0% B, 0-100% B over 3 minutes, then a 1-minute hold at 100% B
Flow: 0.8 mL/min
Detection: 220 nm
Temperature: 40° C.
LC/MS Condition 4
Column: Waters BEH C18, 2.0×50 mm, 1.7 μm particle
Mobile Phase A: 5:95 acetonitrile:water with 10 mM ammonium acetate
Mobile Phase B: 95:5 acetonitrile:water with 10 mM ammonium acetate
Gradient: 0% B, 0-100% B over 3 minutes, then a 0.5-minute hold at 100% B
Flow: 1 mL/min
Detection: UV at 220 nm
Temperature: 50° C.

EXAMPLE B-1

EXAMPLE B-1

Step a

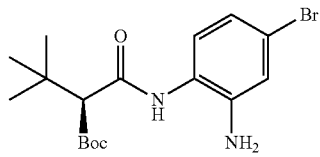

To a solution of 4-bromobenzene-1,2-diamine (2.5 g, 13.37 mmol) in DCM (30 mL) was added (S)-2-((tert-butoxycarbonyl)amino)-3,3-dimethylbutanoic acid (3.09 g, 13.37 mmol), DIPEA (2.334 mL, 13.37 mmol) and HATU (5.08 g, 13.37 mmol). The reaction mixture was stirred at room temperature for 18 h. The reaction mixture was diluted with water and extracted with DCM. The organic phase was washed with brine, dried over Na$_2$SO$_4$, filtered and concentrated. The crude material was purified by ISCO using 40 g Redisep silica column, CHCl$_3$/MeOH as eluant to obtain (S)-tert-butyl (1-((2-amino-4-bromophenyl)amino)-3,3-dimethyl-1-oxobutan-2-yl) carbamate (1.82 g) as yellow solid. LC (Condition 1): R$_t$=2.13 min. LC/MS: Anal. Calcd. for [M+H$_2$O]$^+$ C$_{17}$H$_{27}$BrN$_2$O$_4$: 402.12; found 402.2. $^1$H NMR (DMSO-d$_6$, δ=2.50 ppm, 400 MHz): δ 9.35-9.21 (m, 1H), 7.07 (d, J=8.5 Hz, 1H), 6.91 (d, J=2.0 Hz, 1H), 6.80-6.60 (m, 1H), 5.25-5.01 (m, 2H), 4.07-3.89 (m, 1H), 1.52-1.34 (m, 9H), 1.02-0.86 (m, 9H).

EXAMPLE B-1

Step b

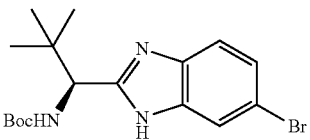

Acetic acid (15 mL) was added to (S)-tert-butyl (1-((2-amino-4-bromo phenyl)amino)-3,3-dimethyl-1-oxobutan-2-yl)carbamate (1.8 g, 4.50 mmol) and the reaction mixture was heated to 65° C. for overnight. The volatile component was removed in vacuo, and the residue was co-evaporated with dry CH$_2$Cl$_2$ (2×15 mL). The organic phase was washed with saturated NaHCO$_3$ solution, brine, dried over Na$_2$SO$_4$ and concentrated to obtain (S)-tert-butyl (1-(6-bromo-1H-benzo[d] imidazol-2-yl)-2,2-dimethyl propyl)carbamate (1.68 g) as yellow solid. LC (Condition 1): R$_t$=2.19 min.

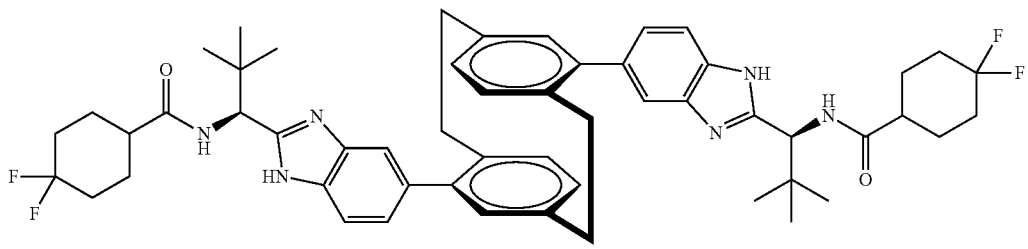

LC/MS: Anal. Calcd. for [M+H]+ $C_{17}H_{25}BrN_3O_2$: 381.11; found 382.2. $^1$H NMR (DMSO-$d_6$, δ=2.50 ppm, 300 MHz): δ 12.46-12.27 (m, 1H), 7.82-7.65 (m, 1H), 7.59-7.41 (m, 1H), 7.29 (dt, J=1.9, 8.5 Hz, 1H), 7.12-6.90 (m, 1H), 4.64 (d, J=9.8 Hz, 1H), 1.44-1.27 (m, 9H), 0.88 (br. s., 9H).

EXAMPLE B-1

Step c

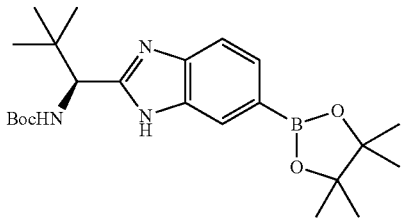 [SMILES: CC(C)(C)OC(=O)N[C@H](c1nc2ccc(B3OC(C)(C)C(C)(C)O3)cc2[nH]1)C(C)(C)C]

To a solution of (S)-tert-butyl (1-(6-bromo-1H-benzo[d]imidazol-2-yl)-2,2-dimethyl propyl)carbamate (1.57 g, 4.11 mmol) in dioxane (25 mL) was added bis (pinacolato) diboron (1.564 g, 6.16 mmol) and potassium acetate (1.209 g, 12.32 mmol). The reaction mixture was purged with argon for 10 min then PdCl$_2$(dppf) (0.150 g, 0.205 mmol) was added to the above reaction mixture and again purged with argon for 5 min. The reaction mixture was heated to 90° C. for overnight. The reaction mixture was diluted with water (15 ml) and extracted with EtOAc (2×25 ml). The combined organic phase was washed with brine, dried over Na$_2$SO$_4$ and concentrated in vacuo. The crude material was purified by ISCO using 40 g Redisep column, hexane/ethyl acetate as eluant to afford (S)-tert-butyl (2,2-dimethyl-1-(6-(4,4,5,5-tetramethyl-1,3,2-dioxaborolan-2-yl)-1H-benzo[d]imidazol-2-yl)propyl) carbamate (1.35 g) as yellow solid. LC (Condition 1): $R_t$=2.21 min. LC/MS: Anal. Calcd. for [M+H]+ $C_{23}H_{37}BN_3O_4$: 430.29; found 430.4. $^1$H NMR (CD$_3$OD, δ=3.34 ppm, 400 MHz): δ 7.98 (s, 1H), 7.65 (dd, J=1.0, 8.5 Hz, 1H), 7.53 (d, J=8.5 Hz, 1H), 4.73 (br. s., 1H), 1.37 (s, 12H), 1.24 (m, 9H), 1.01 (s, 9H).

EXAMPLE B-1

Step d

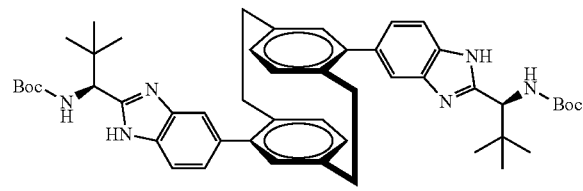

To a solution of (S)-tert-butyl (2,2-dimethyl-1-(6-(4,4,5,5-tetramethyl-1,3,2-dioxaborolan-2-yl)-1H-benzo[d]imidazol-2-yl)propyl)carbamate (1.114 g, 2.59 mmol) and 4,16-dibromo[2,2]paracyclophane (0.38 g, 1.038 mmol) in dioxane (10 mL) was added Cs$_2$CO$_3$ (0.845 g, 2.59 mmol) in water (2 mL) and degassed for 10 min. PdCl$_2$(dppf) (0.038 g, 0.052 mmol) was added to the above reaction mixture and again degassed for 5 min. The reaction mixture was heated to 90° C. for 12 h. Then the reaction mixture was filtered to get Example B-1 Step d which was taken for next step without further purification. LC (Condition 1): $R_t$=2.54 min. LC/MS: Anal. Calcd. for [M+H]+ $C_{50}H_{63}N_6O_4$: 811.49; found 811.6. $^1$H NMR (DMSO-$d_6$, δ=2.50 ppm, 300 MHz): δ 12.36 (br. s., 2H), 7.85-7.52 (m, 4H), 7.32 (d, J=7.9 Hz, 2H), 7.05 (br. s., 2H), 6.89-6.67 (m, 4H), 6.54 (br. s., 2H), 4.72 (d, J=8.7 Hz, 2H), 3.57-3.44 (m, 2H), 3.07 (br. s., 2H), 2.83 (br. s., 2H), 2.65 (br. s., 2H), 1.36 (s, 18H), 1.08-0.91 (m, 18H).

EXAMPLE B-1

Step e

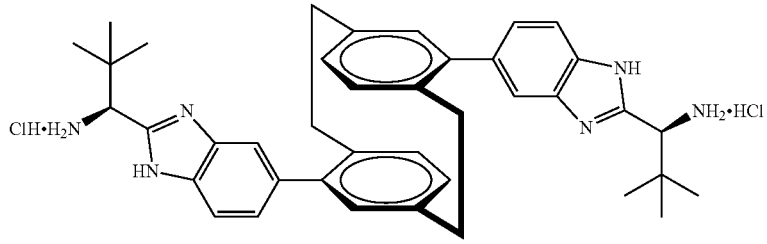

HCl in dioxane (4 mL, 24.00 mmol) was added to Example B-1 Step d (0.1 g, 0.102 mmol), and the reaction mixture was allowed to stir at RT for 2 h. Completion of the reaction was monitored by LCMS. The volatile component was removed in vacuo and the residue was washed with diethyl ether and dried to afford Example B-1 Step e (0.07 g) as yellow solid. LC (Condition 1): $R_t$=2.54 min. LC/MS: Anal. Calcd. for [M+H]+ $C_{40}H_{47}N_6$: 611.39; found 611.4. $^1$H NMR (CD$_3$OD, δ=3.34 ppm, 400 MHz): δ 7.90 (d, J=13.1 Hz, 2H), 7.83 (d, J=8.5 Hz, 2H), 7.61 (d, J=8.5 Hz, 2H), 6.84 (d, J=6.5 Hz, 2H), 6.78 (s, 2H), 6.70-6.65 (m, 2H), 4.54 (d, J=1.0 Hz, 2H), 3.54-3.46 (m, 2H), 3.18-3.10 (m, 2H), 2.98-2.86 (m, 2H), 2.71 (br. s., 2H), 1.25-1.22 (m, 18H).

To a solution of Example B-1 Step e (0.04 g, 0.053 mmol) in DMF (5 mL) was added 4,4-difluorocyclohexanecarboxylic acid (0.017 g, 0.106 mmol), DIPEA (0.055 mL, 0.317 mmol) and HATU (0.030 g, 0.079 mmol). After being stirred for 2 h at room temperature, the volatile component was removed in vacuo and the residue was dissolved in DCM (10 mL), washed with saturated solution of NH$_4$Cl, 10% NaHCO$_3$ solution, brine, dried over Na$_2$SO$_4$ and concentrated in vacuo. The crude was purified by reverse phase HPLC purification to give Example B-1 as a white solid. LC (Condition 1): $R_t$=2.37 min. LC/MS: Anal. Calcd. for [M+H]+ $C_{54}H_{63}F_4N_6O_2$: 903.49; found 903.4. $^1$H NMR (DMSO-d$_6$, δ=2.50 ppm, 400 MHz): δ 12.53-12.32 (m, 2H), 8.41-8.21 (m, 2H), 7.84-7.50 (m, 4H), 7.43-7.24 (m, 2H), 6.90-6.67 (m, 4H), 6.60-6.44 (m, 2H), 5.14-4.97 (m, 2H), 3.44 (br. s., 2H), 3.08 (br. s., 2H), 2.93-2.77 (m, 2H), 2.73-2.56 (m, 4H), 2.20-1.98 (m, 3H), 1.96-1.49 (m, 13H), 1.02 (s, 18H).

The following examples were prepared from Example B-1 Step e, and appropriate acid precursors by employing the procedures described for the synthesis of Example B-1. The resulting products were purified by preparatory HPLC (CH$_3$CN/H$_2$O/NH$_4$OAc).

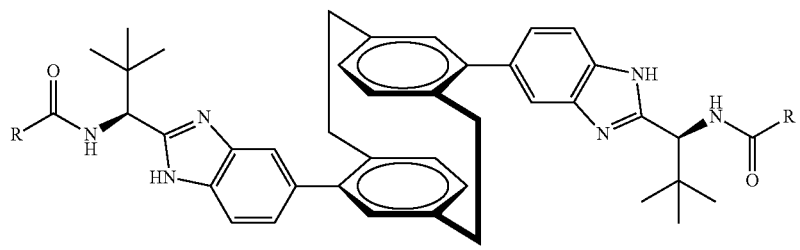

| Example | R | LC & LC/MS data |
|---|---|---|
| B-2 (Diastereomeric mixture) | (cyclopropyl with -C(CH$_3$)OH group) | LC (Condition 1): R$_t$ = 2.15 min. LC/MS: Anal. Calcd. for [M + H]$^+$ C$_{52}$H$_{63}$N$_6$O$_4$: 835.49; found 835.6. $^1$H NMR (MeOD, δ = 3.34 ppm, 300 MHz): δ 7.86-7.59 (m, 4 H), 7.43 (d, J = 8.3 Hz, 2 H), 6.86-6.57 (m, 6 H), 5.12 (s, 1 H), 5.01 (d, J = 2.6 Hz, 1 H), 3.62-3.39 (m, 4 H), 3.18-3.00 (m, 2 H), 2.95-2.78 (m, 2 H), 2.72 (d, J = 8.1 Hz, 2 H), 1.49-1.32 (m, 6 H), 1.31-1.06 (m, 21 H), 1.04-0.74 (m, 5 H), 0.56 (br. s., 2 H) |
| B-3 | (tert-butyl) | LC (Condition 1): R$_t$ = 3.01 min. LC/MS: Anal. Calcd. for [M + H]$^+$ C$_{50}$H$_{63}$N$_6$O$_2$: 779.5; found 779.0. $^1$H NMR (MeOD, δ = 3.34 ppm, 400 MHz): δ 7.94-7.55 (m, 4 H), 7.49 (dd, J = 1.5, 8.5 Hz, 2 H), 6.80 (d, J = 8.0 Hz, 2 H), 6.77-6.74 (m, 2 H), 6.67 (d, J = 8.0 Hz, 2 H), 5.25-5.21 (m, 2 H), 3.54 (ddd, J = 4.0, 9.7, 13.4 Hz, 2 H), 3.16-3.05 (m, 2 H), 2.93-2.84 (m, 2 H), 2.72 (ddd, J = 4.5, 9.5, 13.6 Hz, 2 H), 1.29 (s, 9 H), 1.28 (s, 9 H), 1.09 (s, 18 H) |
| B-4 | (4,4-difluoro-tetrahydropyran carbonyl) | LC (Condition 2): R$_t$ = 2.52 min. LC/MS: Anal. Calcd. for [M + H]$^+$ C$_{54}$H$_{63}$F$_4$N$_6$O$_4$: 935.48; found 935.47. $^1$H NMR (600 MHz, DMSO-d$_6$) δ 12.68-12.51 (m, 2H), 7.78 (m, 3H), 7.74-7.68 (m, 1H), 7.65-7.57 (m, 2H), 7.37-7.29 (m, 2H), 6.83-6.74 (m, 2H), 6.73-6.66 (m, 2H), 6.56-6.45 (m, 2H), 5.14-5.02 (m, 2H), 3.98-3.85 (m, 3H), 3.83-3.73 (m, 2H), 3.11-2.99 (m, 2H), 2.86-2.76 (m, 2H), 2.69-2.55 (m, 2H), 2.13 (br. s., 4H), 1.88-1.75 (m, 2H), 1.75-1.64 (m, 2H), 1.46/1.45 (2 s, 6H), 1.01/0.99 (2 s, 18H). |
| B-5 | (cyclopropyl carbonyl with NH-CH$_2$CF$_3$) | LC (Condition 2): R$_t$ = 2.44 min. LC/MS: Anal. Calcd. for [M + H]$^+$ C$_{52}$H$_{59}$F$_6$N$_8$O$_2$: 941.47; found 941.50. $^1$H NMR (600 MHz, DMSO-d$_6$) δ 12.61-12.46 (m, 2H), 8.41-8.33 (m, 2H), 7.87-7.75 (m, 1H), 7.73 (dd, J = 13.0, 8.3 Hz, 1H), 7.63-7.54 (m, 2H), 7.37-7.33 (m, 1H), 7.29 (t, J = 8.1 Hz, 1H), 6.87-6.80 (m, 1H), 6.79-6.70 (m, 3H), 6.56-6.48 (m, 2H), 5.02 (br. d, J = 9.5 Hz, 2H), 3.55-3.46 (m, 2H), 3.22 (d, J = 7.9 Hz, 2H), 3.17 (d, J = 5.1 Hz, 1H), 3.06-3.05 (m, 1H), 3.12-3.02 (m, 2H), 2.87-2.79 (m, 2H), 2.66-2.58 (m, 2H), 1.20-1.13 (m, 2H), 1.04-0.95 (m, 24H) |

EXAMPLE Y-1 to Y-5

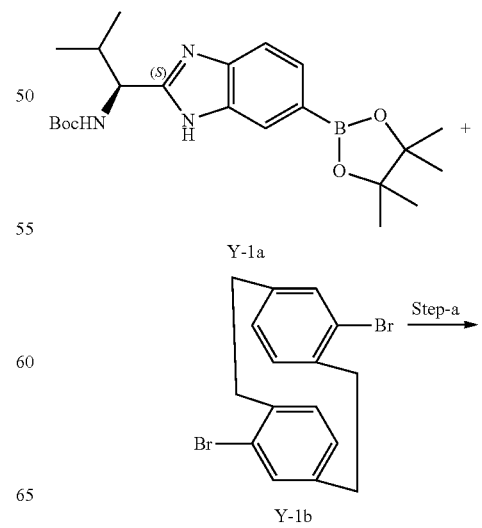

-continued

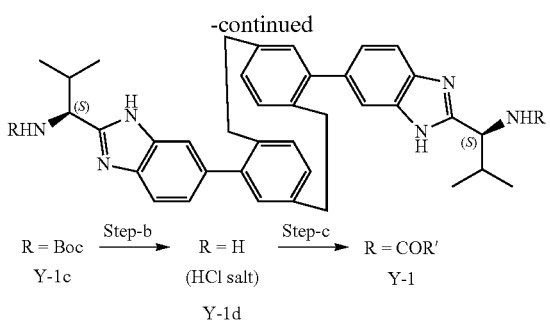

R = Boc →Step-b→ R = H →Step-c→ R = COR'
Y-1c           (HCl salt)           Y-1
              Y-1d Step-a:

To a solution of boronate Y-1a (0.80 g, 1.93 mmol), cyclophane Y-1b (0.25 g, 0.683 mmol) in dioxane (8 mL) was added $Cs_2CO_3$ (0.70 g, 2.148 mmol) in water (2 mL), the mixture was degassed for 10 min and $PdCl_2(dppf)$ (0.025 g, 0.034 mmol) was added to the above reaction mixture and again degassed for 5 min. Reaction mixture was heated to 90° C. for 18 h, cooled to ambient temperature, diluted with EtOAc and filtered, and dried to afford Y-1c as a grey solid (0.45 g). LC (Condition 3): $R_t$=2.79 min. LC/MS: Anal. Calcd. for $C_{48}H_{58}N_6O_4$: 782.45; found 783.61 $[M+H]^+$.

Step b:

Bis-carbamate Y-1c was deprotected to Y-1d (HCl salt) according to the procedure described in Example 1 step e. LC (Condition 3): $R_t$=2.79 min. LC/MS: Anal. Calcd. for $C_{38}H_{42}N_6$.4 HCl: 582.78. found 583.45 $[M+H]^+$.

Step c:

To a mixture of Y-1d (HCl salt) (30 mg, 0.041 mmol) and 4,4-difluorocyclohexanecarboxylic acid (18 mg, 0.110 mmol) in DCM (1 mL) and acetonitrile (1 mL) was added DIPEA (0.1 mL, 0.573 mmol) and TBTU (30 mg, 0.093 mmol). The reaction mixture was stirred at RT for 45 min, diluted with MeOH (1 mL), concentrated and purified by prep HPLC ($H_2O/CH_3CN/NH_4OAc$) to afford Example Y-1. Example Y-2 to Y-5 were prepared similarly from appropriate carboxylic acid precursors, the synthesis of which is reported in the art. Note that the acid precursor used in the preparation of Example Y-4 was a racemate mixture with its hydroxyl and carboxyl moieties cis to each other.

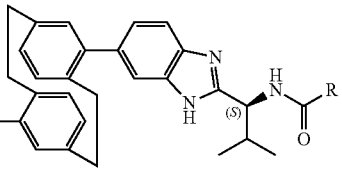

| Example | R | |
|---|---|---|
| Y-1 | 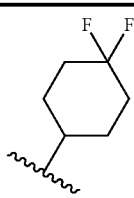 | LC (Condition 4): $R_t$ = 2.28 min. LC/MS: Anal. Calcd. for $C_{52}H_{58}F_4N_6O_2$: 874.456; found 876.0 $[M + H]^+$ |
| Y-2 | 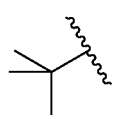 | LC (Condition 4): $R_t$ = 2.35 min. LC/MS: Anal. Calcd. for $C_{48}H_{58}N_6O_2$: 750.46; found 751.46. $[M + H]^+$ |
| Y-3 | [structure: 4,4-difluoro-2-methyltetrahydropyran] | LC (Condition 4): $R_t$ = 2.42 min. LC/MS: Anal. Calcd. for $C_{52}H_{58}F_4N_6O_4$: 906.446; found, 907.45 $[M + H]^+$ |
| Y-4 (Mixture of diastereomers) | [structure: HO-cyclohexyl-Me (OH & Me are cis)] | LC (Condition 4): $R_t$ = 2.26 min. LC/MS: Anal. Calcd. for $C_{54}H_{66}N_6O$: 862.515; found 864.1 $[M + H]^+$ |
| Y-5 | [structure: methoxy-t-butyl] | LC (Condition 4): $R_t$ = 2.79 min. LC/MS: Anal. Calcd. for $C_{50}H_{62}N_6O_4$: 810.483; found, 811.65 $[M + H]^+$ |

BIOLOGICAL ACTIVITY

The NS5A synergistic inhibitory effect of test compounds can be determined using various amounts of an NS5A-targeting compound with titration of a second compound of interest. Both the NS5A-targeting compound and the second compound of interest, when tested individually versus HCV variants, are understood to be essentially inactive or weakly active and only regain synergistic inhibitory potency of 3-fold or greater inhibition when tested in combination versus HCV variants. In one embodiment, compound BMS-790052, as an NS5A-targeting compound, can be held constant at a fixed concentration of 200 nM with subsequent titration of the test compound on a variant of HCV. In one embodiment, the HCV genotype strain can be genotype 1a containing a change at amino acid 30 of the NS5A protein consisting of glutamine to glutamate. The test compound can be chosen from compounds listed above or from others present in the literature. One skilled in the art can readily test compounds in the HCV replicon cell based assay as has been demonstrated previously in the art and one can readily determine the effective concentration for 50% inhibition ($EC_{50}$) of a particular compound.

For illustration, Compound P-55, which is noted below, can be titrated in the HCV replicon cell-based assay consisting of the genotype-1a variant with glutamine 30 changed to glutamate in the NS5A protein. Titration of BMS-790052 singly would yield an $EC_{50}$ value ~200 nM while titration of P-55 singly would yield an $EC_{50}$ value >200 nM. The titration of P-55 in the presence of a fixed amount of BMS-790052 at 200 nM afforded an $EC_{50}$ values of ~2 nM for P-55 demonstrating a synergistic inhibitory effect for the combination of >100-fold. Similarly, the titration of BMS-790052 in the presence of a fixed amount of P-55 at 200 nM afforded an $EC_{50}$ values of ~2 nM for BMS-790052, demonstrating a reciprocal synergistic inhibitory effect ~100-fold for the combination (PCT/US2011/043785, filed Jul. 13, 2011), Table 3). Additional compounds can be tested in a similar manner and a ranking of synergist activities determined; these rankings for the genotype 1a Q→E variant are shown for selected compounds in the table below.

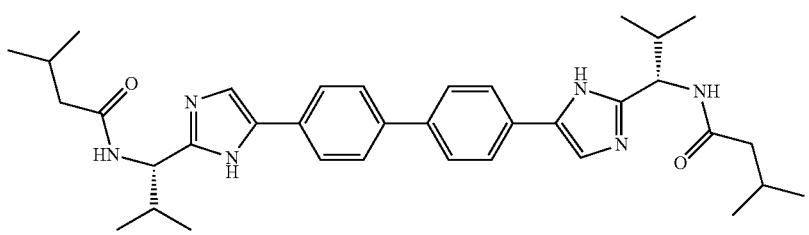

Compound P55

It is understood that the genotype is not limited to the genotype 1a variant but can encompass all genotypic variants of HCV including but not limited to HCV variants of 1b, 2a, 3a, 4a, 5a, 6a as demonstrated in commonly owned WO2012/009394. It is also understood that the synergy effect is not limited to BMS-790052 or P-55 combinations but can be derived from other combinations of NS5A-targeting compounds that by themselves have reduced or no potency towards HCV variants.

| Example | Fold-Synergistic 1a (Q30E) |
|---------|----------------------------|
| B-1 | >100 |
| B-2 | >100 |
| B-3 | >100 |
| B-4 | >100 |
| B-5 | 70x |
| Y-3 | >100x |
| Y-4 | >100x |
| Y-5 | >100x |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is BMS-790052:

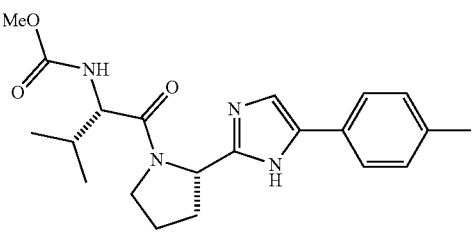

-continued

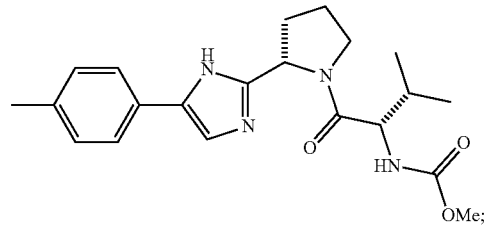

BMS-790052 and wherein the NS5A synergist is a compound of formula (I):

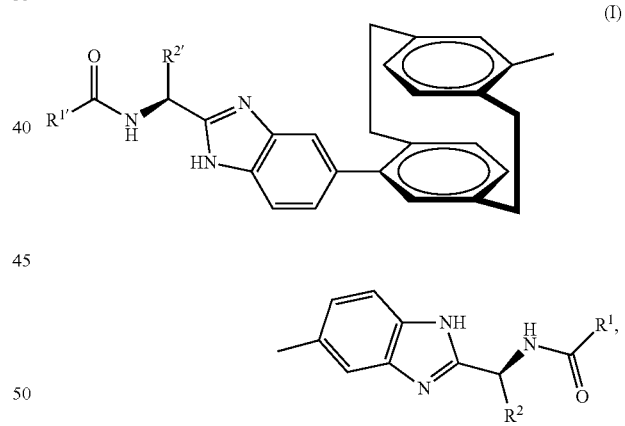

(I)

or a pharmaceutically acceptable salt thereof, wherein $R^1$ and $R^{1'}$ are independently selected from alkoxyalkyl, alkyl, cycloalkyl, and pyranyl, wherein the cycloalkyl and the pyranyl are optionally substituted with one, two, or three substituents independently selected from alkyl, halo, haloalkyl, hydroxy, and hydroxyalkyl; and $R^2$ and $R^{2'}$ are the same or different alkyl groups.

2. The combination of claim 1 wherein the compound of formula (I) is selected from

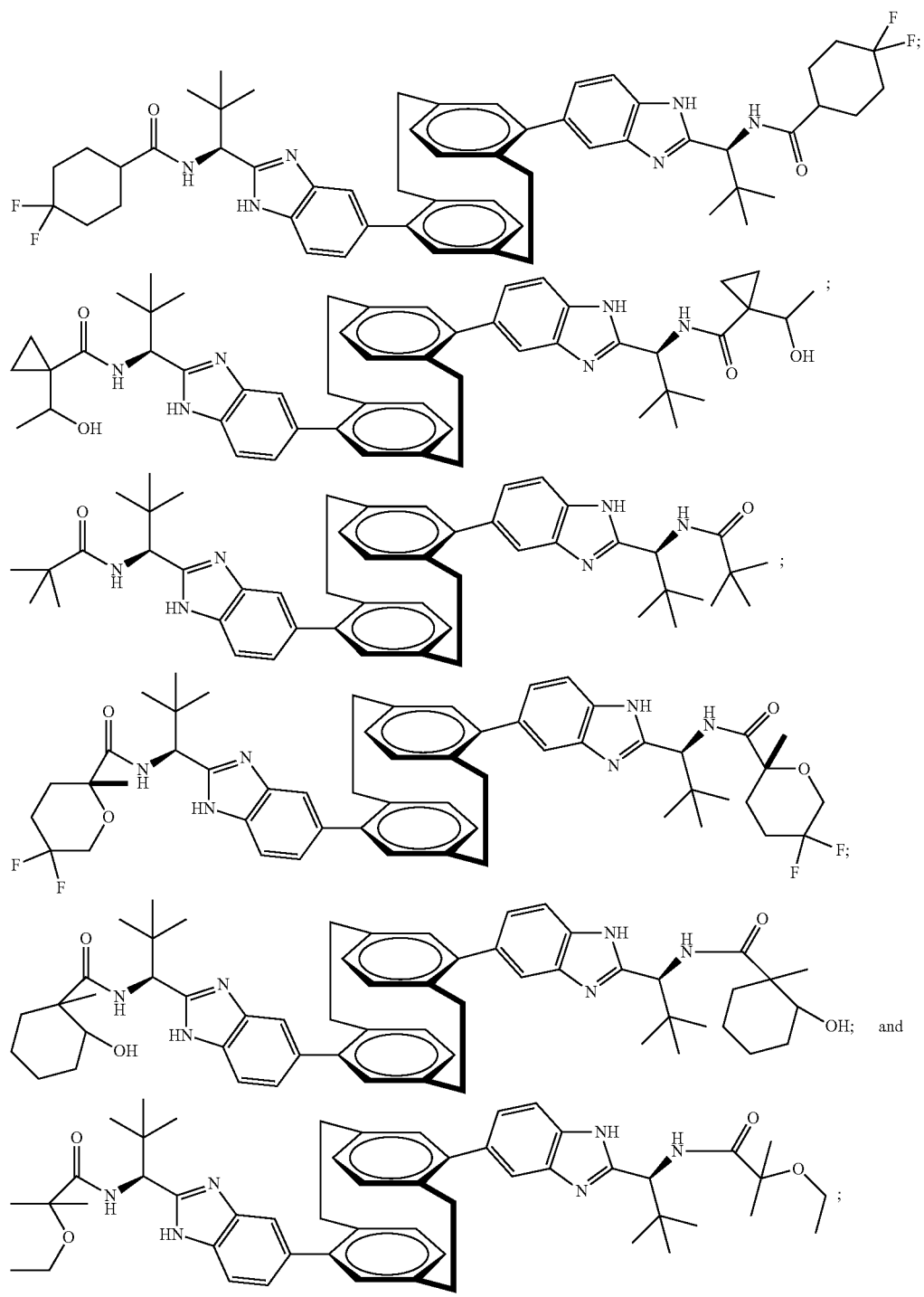

or a pharmaceutically acceptable salt thereof.

3. A composition comprising the combination of claim 1 and one or more pharmaceutically acceptable carriers.

4. The composition of claim 3 further comprising one or two additional compounds having anti-HCV activity.

5. The composition of claim 4 wherein at least one of the additional compounds is an interferon or a ribavirin.

6. The composition of claim 5 wherein the interferon is selected from interferon alpha 2B, pegylated interferon alpha, pegylated interferon lambda, consensus interferon, interferon alpha 2A, and lymphoblastoid interferon tau.

7. The composition of claim 4 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

8. A method of treating an HCV infection in a patient, comprising administering to the patient a therapeutically effective amount of a combination of claim 1, or a pharmaceutically acceptable salt thereof.

9. The method of claim 8 further comprising administering one or two additional compounds having anti-HCV activity prior to, after or simultaneously with the combination, or a pharmaceutically acceptable salt thereof.

10. The method of claim 9 wherein at least one of the additional compounds is an interferon or a ribavirin.

11. The method of claim 10 wherein interferon is selected from interferon alpha 2B, pegylated interferon alpha, pegylated interferon lambda, consensus interferon, interferon alpha 2A, and lymphoblastoid interferon tau.

12. The method of claim 9 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

\* \* \* \* \*